(12) United States Patent
Miyama et al.

(10) Patent No.: US 7,312,372 B2
(45) Date of Patent: *Dec. 25, 2007

(54) ELONGATED ABSORBENT ARTICLE WITH COMPRESSED GROOVE

(75) Inventors: Takuya Miyama, Kagawa (JP); Masataka Kinoshita, Kagawa (JP); Jun Kudo, Kagawa (JP); Kenichiro Kuroda, Kagawa (JP); Tatsuya Tamura, Kagawa (JP); Shimpei Komatsu, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 62 days.

This patent is subject to a terminal disclaimer.

(21) Appl. No.: 11/058,461

(22) Filed: Feb. 14, 2005

(65) Prior Publication Data

US 2005/0148972 A1    Jul. 7, 2005

Related U.S. Application Data

(63) Continuation of application No. PCT/JP03/15390, filed on Dec. 2, 2003.

(30) Foreign Application Priority Data

Dec. 5, 2002    (JP) .............................. 2002-354174

(51) Int. Cl.
*A61F 13/20* (2006.01)

(52) U.S. Cl. ...................... 604/380; 604/378; 604/379; 604/385.01; 604/385.04; 604/381; 604/382; 604/383

(58) Field of Classification Search ................ 604/380, 604/378–379, 385.01, 385.04, 384, 381–383
See application file for complete search history.

(56) References Cited

U.S. PATENT DOCUMENTS

| | | | | |
|---|---|---|---|---|
| 3,575,174 | A | * | 4/1971 | Mogor .................. 604/385.01 |
| 4,397,644 | A | * | 8/1983 | Matthews et al. .......... 604/378 |
| 4,655,759 | A | * | 4/1987 | Romans-Hess et al. 604/385.21 |
| 4,758,240 | A | * | 7/1988 | Glassman ................... 604/379 |
| 4,936,839 | A | * | 6/1990 | Molee et al. ............... 604/378 |
| 5,211,641 | A | * | 5/1993 | Roos et al. ........... 604/385.201 |
| 5,312,386 | A | * | 5/1994 | Correa et al. ............... 604/379 |
| 5,752,947 | A | * | 5/1998 | Awolin ....................... 604/387 |
| 5,921,975 | A | * | 7/1999 | Suzuki et al. .......... 604/385.17 |
| 6,114,597 | A | * | 9/2000 | Romare ...................... 604/378 |
| 6,375,644 | B2 | * | 4/2002 | Mizutani ............... 604/385.01 |
| 6,703,538 | B2 | * | 3/2004 | Lassen et al. ............... 604/378 |

(Continued)

FOREIGN PATENT DOCUMENTS

JP    9-502633    3/1997

(Continued)

*Primary Examiner*—Tatyana Zalukaeva
*Assistant Examiner*—Ginger Chapman
(74) *Attorney, Agent, or Firm*—Darby & Darby P.C.

(57) ABSTRACT

Disclosed is an elongated absorbent article including a liquid absorbent layer. In a region where the liquid absorbent layer is present, compressed grooves are disposed to extend symmetrically about a longitudinal centerline, defining a central region therebetween and side regions laterally outside the central region and adjacent the compressed grooves. The central region includes front, intermediate and rear central regions. The intermediate central region has a widened portion in which the separation distance is larger than in regions positioned forward and rearward thereof. Stiffness of the side regions is lower in portions laterally outside the intermediate central region than in portions laterally outside the front and rear central regions.

6 Claims, 8 Drawing Sheets

U.S. PATENT DOCUMENTS

| | | |
|---|---|---|
| 6,858,771 B2 * | 2/2005 | Yoshimasa et al. .......... 604/380 |
| 6,911,574 B1 * | 6/2005 | Mizutani ..................... 604/380 |
| 7,067,711 B2 * | 6/2006 | Kuroda et al. .............. 604/380 |
| 7,078,583 B2 * | 7/2006 | Kudo et al. ................. 604/380 |
| 7,122,713 B2 * | 10/2006 | Komatsu et al. ............ 604/380 |
| 2002/0004654 A1 * | 1/2002 | Daniels et al. .............. 604/380 |
| 2002/0010449 A1 * | 1/2002 | Mizutani ..................... 604/380 |
| 2002/0052587 A1 * | 5/2002 | Magnusson et al. ........ 604/378 |
| 2003/0018314 A1 * | 1/2003 | Nozaki et al. ........ 604/385.101 |
| 2003/0055392 A1 * | 3/2003 | Tagami et al. .............. 604/378 |
| 2003/0088222 A1 * | 5/2003 | Yoshimasa et al. ......... 604/380 |
| 2003/0093054 A1 * | 5/2003 | Sierri et al. ............ 604/385.04 |
| 2004/0243082 A1 * | 12/2004 | Kinoshita et al. ........... 604/380 |
| 2004/0249355 A1 * | 12/2004 | Tanio et al. ........... 604/385.01 |
| 2004/0260262 A1 * | 12/2004 | Nishitani et al. ...... 604/385.04 |
| 2005/0085783 A1 * | 4/2005 | Komatsu et al. ....... 604/385.04 |
| 2005/0124951 A1 * | 6/2005 | Kudo et al. ................. 604/380 |
| 2005/0148971 A1 * | 7/2005 | Kuroda et al. .............. 604/380 |
| 2005/0148973 A1 * | 7/2005 | Tamura et al. .............. 604/380 |

FOREIGN PATENT DOCUMENTS

| | | |
|---|---|---|
| JP | 2001-095842 | 4/2001 |
| JP | 2001-129018 | 5/2001 |
| JP | 2001-299812 | 10/2001 |

* cited by examiner

ELONGATED ABSORBENT ARTICLE WITH COMPRESSED GROOVE

BACKGROUND OF THE INVENTION

1. Field of the Invention

The present invention relates to an absorbent article suitable for absorbing menstrual blood and so on discharged from a woman's genital organ, more particularly, relates to an elongated absorbent article intended to cover the wearer's body from a vaginal opening to buttocks.

2. Description of the Related Art

Absorbent articles intended to absorb menstrual blood discharged from a woman's genital organ are typically constructed to include a liquid absorbent layer, a liquid-permeable topsheet covering the skin surface of the liquid absorbent layer, and a liquid-impermeable backsheet covering the garment surface of the liquid absorbent layer, and generally, they are worn with the backsheet adhered to an inner side of a groin piece of an undergarment through a pressure-sensitive adhesive layer.

In such an absorbent article, the function of certainly collecting menstrual blood applied to the skin surface is required so as to prevent lateral leakage of liquid and rearward leakage of liquid from the absorbent article.

Particularly in an absorbent article that is intended to be worn by a woman during menstruation while sleeping, required is not only prevention of lateral leakage of menstrual blood from the absorbent article but certain absorption of menstrual blood trying to flow along the wearer's body toward the anus and the cleft of the buttocks or trying to flow along the skin surface of the absorbent article rearwardly without causing any leakage. Accordingly, such an absorbent article for nighttime use is elongated more than absorbent articles for daytime use so that its skin surface can cover a large area from a mons pubis which is anterior to the vaginal opening to the buttocks which is posterior to the anus.

Japanese Unexamined Patent Publication No. 2001-95842 (Patent Publication 1) discloses an elongated sanitary napkin which is intended for nighttime use. In this sanitary napkin, the skin surface is provided with a circular emboss and the region surrounded by the circular emboss is a high-center portion, wherein the high-center portion is elongated longitudinally of the sanitary napkin. At a position between front and rear regions, the lateral separation distance between opposing portions of the circular emboss is increased to provide swelling embosses. On its skin surface, furthermore, longitudinally extending gathered cuffs are provided at both sides thereof, along with elastically extensible members for raising the gathered cuffs.

The invention disclosed in Patent Publication 1 aims at swelling a portion having the swelling embosses toward the wearer's body by making use of a longitudinal shrinkage force of the elastically extensible members exerted on the sanitary napkin so that the portion having the swelling embosses may fit on the wearer's body.

On the other hand, Japanese Unexamined Patent Publication No. 2001-129018 (Patent Publication 2) discloses an absorbent article whose skin surface is provided with leakage preventing grooves which are mutually connected to surround an elongated liquid receiving region, wherein the mutually connected leakage preventing grooves are doubled in a rear portion. This invention aims at preventing rearward leakage of menstrual blood from the absorbent article by doubling the mutually connected leakage preventing grooves.

In the invention disclosed in Patent Publication 1, however, stiffness of the sanitary napkin in the portion having the swelling embosses differs little from that in portions forward and rearward thereof. Therefore, when the longitudinal shrinkage force of the elastically extensible members is exerted, the portion having the swelling embosses tends to be folded on its laterally extending fold line, so that the portion having the swelling embosses is easily folded toward the wearer's body while swelling in a direction perpendicular to the cleft of the buttocks. That is, because the portion having the swelling embosses is folded while being widened in a direction perpendicular to the direction of recesses anterior and posterior to the perineum, it is difficult for the skin surface of the sanitary napkin to come into close contact with the perineum and portions anterior and posterior thereto without fail.

In the sanitary napkin disclosed in Patent Publication 1, moreover, the skin surface is sometimes curved away from the wearer's body due to the longitudinal elastic shrinkage force of the elastically extensible members. When thus deformed, the portion having the swelling embosses is easily separated from the wearer's body to leave a space between the skin surface and the perineum and portions anterior and posterior thereto.

Furthermore, since the sanitary napkin disclosed in Patent Publication 1 is provided with almost constant stiffness over the region from the intermediate portion having the swelling embosses to the rear portion, the whole body tends to deform freely over the region from the intermediate portion to the rear portion. Therefore, when movement of the buttocks exerts an external force on the intermediate and rear portions, the sanitary napkin is twisted or wrinkled to increase the possibility of leaving a space between the wearer's body and the skin surface.

On the other hand, since the mutually connected leakage preventing grooves disclosed in Patent Publication 2 are doubled in the rear portion, stiffness is increased only in the rear portion with the double portion of the mutually connected leakage preventing grooves. Therefore, the absorbent article is easily folded at the boundary between the single portion and the double portion of the mutually connected leakage preventing grooves and separated from the wearer's body at this portion, i.e., portion which is intended to face the woman's perineum. This results in that menstrual blood tends to flow rearwardly along the wearer's body, so that the cause of rearward liquid leakage cannot be basically eliminated.

SUMMARY OF THE INVENTION

The present invention has been worked out in view of the shortcomings in the prior art set forth above. It is therefore an object of the present invention to provide an absorbent article whose skin surface can conform to irregularities of the wearer's body, e.g., the woman's perineum and portions anterior and posterior thereto, effectively preventing rearward leakage of menstrual blood.

Another object of the present invention is to provide an absorbent article whose front portion and rear portion can easily move independently from each other in accordance with movement of the wearer's body, keeping in contact with the crotch and the buttocks, respectively.

According to a first aspect of the present invention, there is provided an elongated absorbent article comprising a liquid absorbent layer, the absorbent article having a skin surface and a garment surface, wherein in a region where the liquid absorbent layer is present, compressed grooves where the skin surface is recessed toward the garment surface are disposed to extend symmetrically about a longitudinal centerline of the absorbent article, defining a central region between the compressed grooves and side regions laterally outside the central region and adjacent the compressed grooves, the central region including a front central region at a front side in a longitudinal direction of the absorbent article, a rear central region at a rear side in the longitudinal direction, and an intermediate central region between the front and rear central regions, wherein separation distance between the compressed grooves gradually increases from the front central region to the intermediate central region and also from the rear central region to the intermediate central region so that the intermediate central region has a widened portion in which the separation distance is larger than in regions positioned forward and rearward thereof, wherein stiffness of the side regions is lower in portions laterally outside the intermediate central region than in portions laterally outside the front and rear central regions.

This absorbent article has high stiffness at both sides of the front central region and at both sides of the rear central region, but low stiffness at both sides of the intermediate central region with the widened portion. When the absorbent article is worn, therefore, a pressure from the thighs is laterally exerted on both sides of the front central region and both sides of the rear central region, and at the same time, the widened portion of the intermediate central region is longitudinally pressed by the front and rear side regions of high stiffness, so that the intermediate central region is deformed to bulge toward the wearer's body while being pressed and supported from four directions. As a result, the intermediate central region entirely bulges, without being completely folded, and rises up toward the wearer's body to fit on the woman's perineum and into recesses anterior and posterior thereto, so that menstrual blood discharged from the vaginal opening can be easily collected by the intermediate central region and rearward liquid leakage can be easily prevented.

In addition, since the front portion having the front central region and the rear portion having the rear central region are provided with some degree of stiffness while the intermediate portion therebetween is provided with low stiffness, the front portion and the rear portion can move independently from each other with boundary at the intermediate portion. Accordingly, both the front and rear portions can follow the movement of the wearer's body without being twisted or wrinkled and space is hardly left between the skin surface of the whole absorbent article and the wearer's body, so that the effect of preventing leakage of menstrual blood can be improved.

In the first aspect of the present invention, for example, the front central region, the rear central region and the intermediate central region are intended to face a vaginal opening, an anus and a perineum of a wearer, respectively.

Since the intermediate central region can be deformed to bulge toward the wearer's body not only laterally but also longitudinally, as set forth above, the intermediate central region can easily fit into a deep recess between the labia majora and the perineum, and further into a recess which is posterior to the perineum and adjacent to the anus, so that menstrual blood discharged from the vaginal opening and trying to move toward the anus can be effectively absorbed by the liquid absorbent layer in the intermediate central region and prevented from leaking out rearwardly from the absorbent article.

In the first aspect of the present invention, preferably, when measured for areas each traversed by one compressed groove to overlap with one of the front, intermediate and rear central regions and one side region adjacent thereto, longitudinal bending stiffness is lower in the area overlapping with the intermediate central region than in the area overlapping with the front central region and in the area overlapping with the rear central region.

In order to thus provide a difference in stiffness, density of the liquid absorbent layer in the side regions may be lower in the portions laterally outside the intermediate central region than in the portions laterally outside the front and rear central regions.

According to a second aspect of the present invention, there is provided an elongated absorbent article comprising a liquid absorbent layer, the absorbent article having a skin surface and a garment surface, wherein in a region where the liquid absorbent layer is present, inner compressed grooves where the skin surface is recessed toward the garment surface are disposed to extend symmetrically about a longitudinal centerline of the absorbent article, defining a central region between the inner compressed grooves, the central region including a front central region at a front side in a longitudinal direction of the absorbent article, a rear central region at a rear side in the longitudinal direction, and an intermediate central region between the front and rear central regions, wherein separation distance between the inner compressed grooves gradually increases from the front central region to the intermediate central region and also from the rear central region to the intermediate central region so that the intermediate central region has a widened portion in which the separation distance is larger than in regions positioned forward and rearward thereof, wherein front and rear outer compressed grooves separate from the inner compressed grooves are disposed in portions laterally outside the front and rear central regions, respectively, to extend symmetrically about the longitudinal centerline, rear ends of the front outer compressed grooves being spaced longitudinally apart from front ends of the rear outer compressed grooves in portions laterally outside the intermediate central region.

In this absorbent article, the front outer compressed grooves and the rear outer compressed grooves themselves function as highly stiff portions positioned forward and rearward of the intermediate central region having the widened portion, which exerts a force toward the wearer's body on the intermediate central region. It should be noted that outer compressed grooves for continuously connecting the rear ends of the front outer compressed grooves to the front ends of the rear outer compressed grooves are not disposed in the portions laterally outside the intermediate central region. However, it is also possible to arrange dot-shaped small compressed portions in such a manner as to connect the rear ends of the front outer compressed grooves to the front ends of the rear outer compressed grooves.

In the second aspect of the present invention, preferably, imaginary extensions, which are extended from the front ends of the rear outer compressed grooves in parallel with the longitudinal centerline, intersect portions of the inner compressed grooves which define the intermediate central region therebetween.

If the imaginary extensions intersect the portions of the inner compressed grooves, when a longitudinal shrinkage force acts on the absorbent article, the rear outer compressed grooves can exert a forward pressure on the widened portion of the intermediate central region and the front outer compressed grooves positioned forward of the intermediate central region can receive the pressure, so that the intermediate central region is pressed and supported from four directions with the four outer compressed grooves positioned forward and rearward thereof, thereby deforming to bulge as a whole to fit on the wearer's body.

Also in the second aspect of the present invention, the front central region, the rear central region and the intermediate central region may be intended to face a vaginal opening, an anus and a perineum of a wearer, respectively.

In the second aspect of the present invention, density of the liquid absorbent layer may be higher in portions between the inner compressed grooves and the front outer compressed grooves and in portions between the inner compressed grooves and the rear outer compressed grooves than in portions laterally outside portions of the inner compressed grooves which define the intermediate central region therebetween.

In this construction, not only the front outer compressed grooves but also the portions between the inner compressed grooves and the front outer compressed grooves can provide high stiffness and not only the rear outer compressed grooves but also the portions between the inner compressed grooves and the rear outer compressed grooves can likewise provide high stiffness, so that the intermediate central region can be pressed and supported from four directions with the outer compressed grooves and the highly stiff portions, deforming toward the wearer's body.

In both the first and second aspects of the present invention, preferably, elastic members are disposed symmetrically about the longitudinal centerline to exert an elastic shrinkage force in the longitudinal direction so that action ends positioned forward of the intermediate central region and action ends positioned rearward of the intermediate central region are attracted to each other.

If such a longitudinal elastic shrinkage force acts on the absorbent article, highly stiff portions forward and rearward of the intermediate central region can exert a force forwardly and rearwardly on the intermediate central region, resulting in that the intermediate central region can be easily deformed to bulge toward the wearer's body.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to devices which are intended to be worn in the crotch of a wearer to absorb various exudates discharged from the wearer's body, such as menstrual blood, urine, and vaginal discharge, but in the following embodiments, the absorbent article is shown embodied in a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "compressed groove" refers to grooves where at least the liquid absorbent layer is highly compressed. In each compressed groove that is formed to extend continuously, density of the liquid absorbent layer may be uniform at the groove bottom or portions of different densities may alternate with each other at the groove bottom. In either case, the density of the liquid absorbent layer is higher at the bottom of the compressed groove than at regions other than the compressed groove.

As used herein, the term "longitudinal centerline" refers to a line which extends longitudinally to divide the absorbent article laterally in two. On the other hand, the term "lateral reference line" does not necessarily refer to a line which extends laterally to divide the absorbent article longitudinally in two, but refers to a line which extends laterally to cross a longitudinal center of a portion intended to be brought into contact with the vaginal opening during wear.

In the following embodiments, the intermediate central region is positioned between the rear ends of the front outer compressed grooves and the front ends of the rear outer compressed grooves. In other words, the intermediate central region refers to an area containing the widened portion where the separation distance between the inner compressed grooves is increased and having a length of 20 to 60 mm in the longitudinal direction of the absorbent article.

Figure 1:
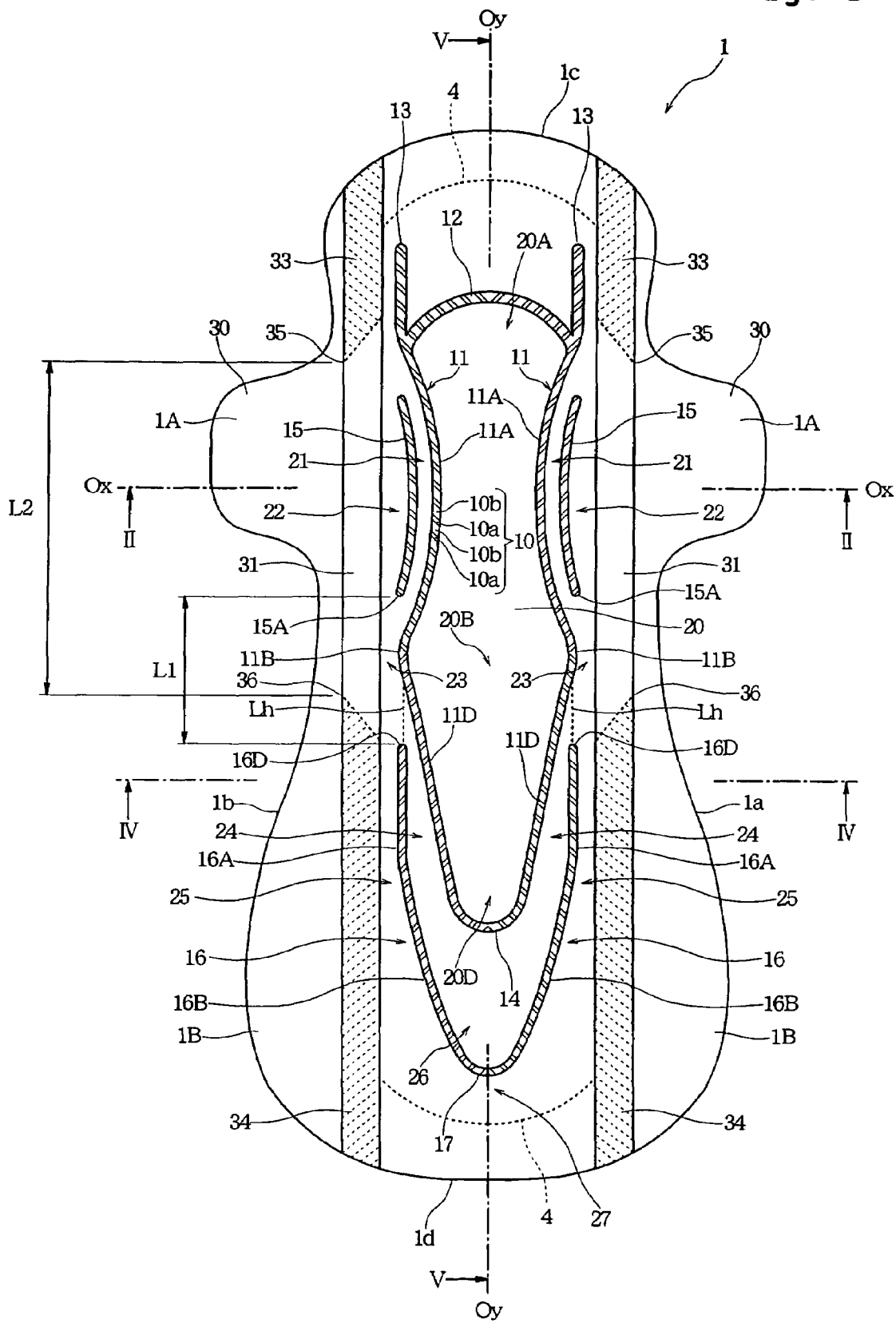
FIG. 1 is a top plan view showing a sanitary napkin as an absorbent article according to a first embodiment of the present invention.
Figure 2:
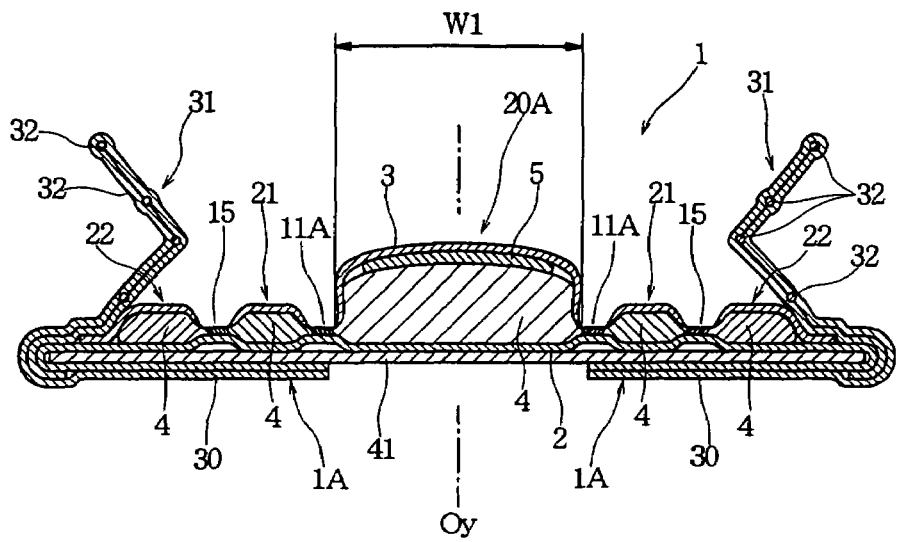
FIG. 2 is a sectional view taken along line II-II (lateral reference line), showing a state where the sanitary napkin of FIG. 1 is attached to a crotch portion of an undergarment.
Figure 3:
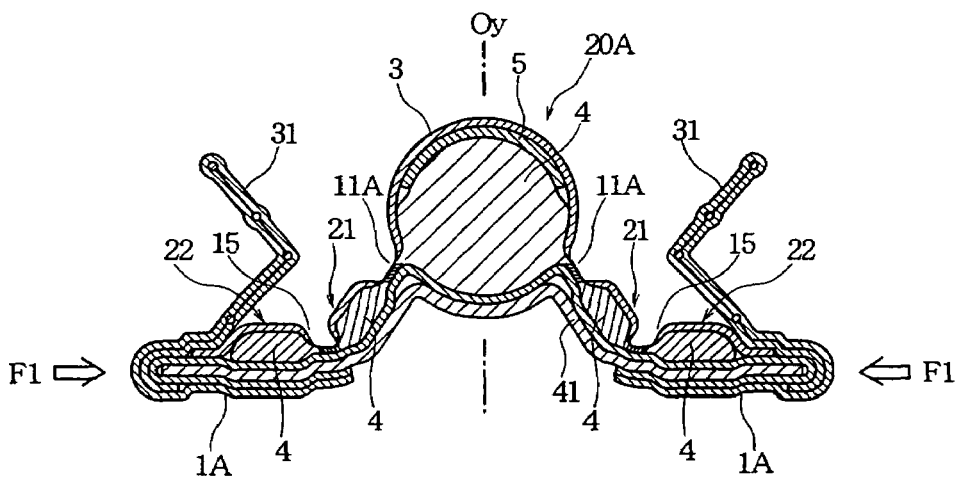
FIG. 3 is a sectional view taken along line II-II, showing a state where the sanitary napkin of FIG. 1 is deformed during wear.
Figure 4:
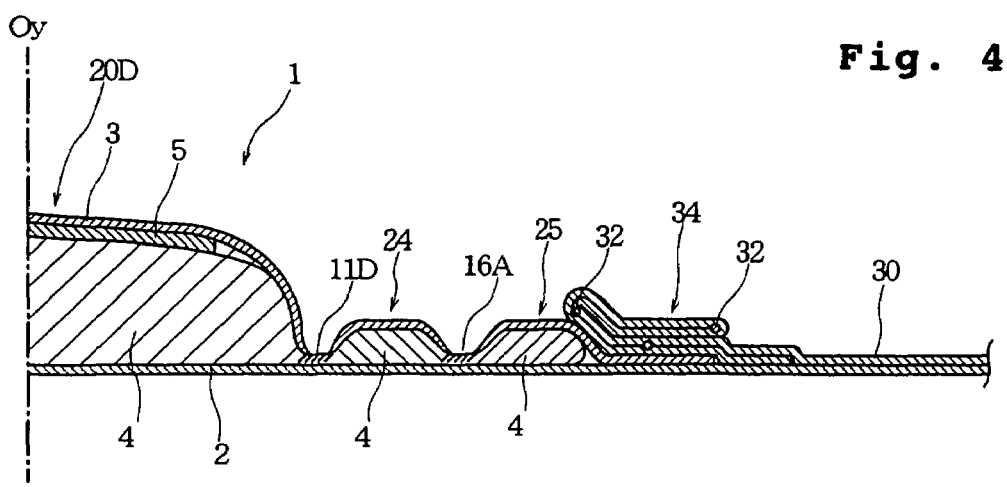
FIG. 4 is a half sectional view of the sanitary napkin of FIG. 1 taken along line IV-IV.
Figure 5:
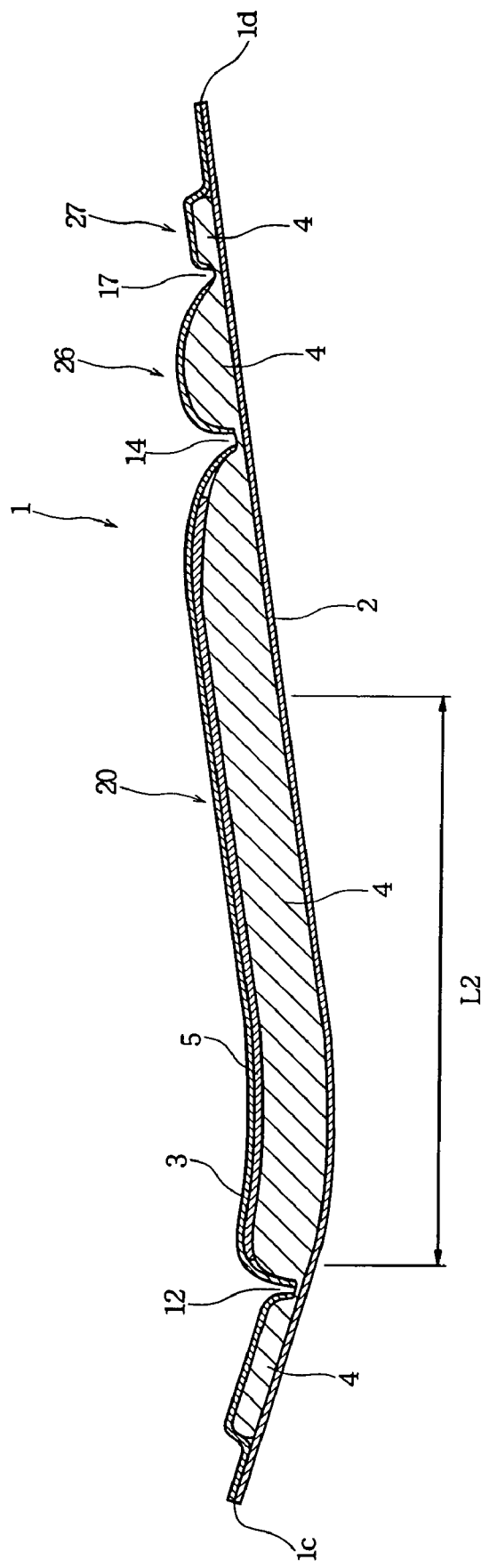
FIG. 5 is a sectional view of the sanitary napkin of FIG. 1 taken along line V-V (longitudinal centerline)

FIG. 1 is a top plan view showing a sanitary napkin 1 as an absorbent article according to a first embodiment of the present invention, wherein the skin surface faces upward; FIG. 2 is a sectional view taken along line II-II (lateral reference line), showing a state where the sanitary napkin of FIG. 1 is attached to a groin piece of an undergarment; FIG. 3 is a sectional view showing a state where the sanitary napkin attached to the groin piece is deformed during wear; FIG. 4 is a half sectional view of the sanitary napkin of FIG. 1 taken along line IV-IV; and FIG. 5 is a sectional view of the sanitary napkin of FIG. 1 taken along line V-V (longitudinal centerline).

The sanitary napkin 1 of FIG. 1 is an elongated sanitary napkin that is suitable for nighttime use by a woman during menstruation, wherein the entire length in the longitudinal direction is from about 200 to 380 mm.

The sanitary napkin 1 has longitudinally extending right and left side edges 1a and 1b that are laterally spaced an equal distance apart from a longitudinal centerline Oy-Oy and outwardly curved front and rear end edges 1c and 1d that are longitudinally spaced apart from a lateral reference line Ox-Ox. The distance from the lateral reference line Ox-Ox to the rear end edge 1d is larger than the distance from the lateral reference line Ox-Ox to the front end edge 1c.

Within a range having a given length in the longitudinal direction and containing the lateral reference line Ox-Ox, the right and left side edges 1a and 1b project laterally outwardly, thereby providing wings 1A and 1A. Rearward of the wings 1A and 1A, furthermore, the right and left side edges 1a and 1b are curved to gradually rearwardly increase the lateral separation distance therebetween, thereby providing rear flaps 1B and 1B.

As shown in the respective sectional views of FIGS. 2, 4 and 5, the sanitary napkin 1 comprises a liquid-impermeable backsheet 2 appearing on the garment surface and a liquid-permeable topsheet 3 appearing on the skin surface. Between the backsheet 2 and the topsheet 3, a liquid absorbent layer 4 is interposed. As indicated by a dotted line in FIG. 1, the liquid absorbent layer 4 extends over a large area from a position just inside the front end edge 1c to a position just inside the rear end edge 1d, but for the wings 1A, 1A and the rear flaps 1B, 1B. As will be described later, basis weight and density of the liquid absorbent layer 4 are different for different portions.

In the sanitary napkin 1, compressed groove 10 is formed in the skin surface by locally pressing and heating at least the topsheet 3 and the liquid absorbent layer 4. More specifically, the compressed groove 10 is formed by embossing with a heating roller in such a manner that after the liquid absorbent layer 4 is stacked on the topsheet 3, a smooth surface roller is applied to a surface of the liquid absorbent layer 4 while a heating roller whose surface has projections arranged in a pattern for embossing is applied to a surface of the topsheet 3 for pressing and heating.

The compressed groove 10 has high-density compressed portions 10a, in which the liquid absorbent layer 4 and the topsheet 3 are pressed until they get almost filmy, and medium-density compressed portions 10b positioned between adjacent high-density compressed portions 10a, in which although doesn't get filmy, the liquid absorbent layer 4 is of a higher density than in portions other than the compressed groove 10. The high-density compressed portions 10a and the medium-density compressed portions 10b alternate with each other in every part of the compressed groove 10 patterned as shown in FIG. 1, providing continuous grooves where the skin surface of the sanitary napkin 1 is recessed toward the side of the backsheet 2.

As shown in FIG. 1, the compressed groove 10 has several distinct compressed grooves indicated by numerals 11-17.

Longitudinally extending inner compressed grooves 11 and 11 are disposed symmetrically about the longitudinal centerline Oy-Oy. The inner compressed grooves 11 and 11 include front curved portions 11A and 11A, inflected portions 11B and 11B and rear oblique portions 11D and 11D. The front curved portions 11A and 11A are curved toward the longitudinal centerline Oy-Oy so that separation distance therebetween is minimum at the lateral reference line Ox-Ox. As the front curved portions 11A and 11A extend rearwardly (toward the rear end edge 1d) from the lateral reference line Ox-Ox, the separation distance between the inner compressed grooves 11 and 11 gradually increases. Then, the separation distance becomes largest at the inflected portions 11B and 11B and gradually decreases rearwardly from the inflected portions 11B and 11B to provide the rear oblique portions 11D and 11D.

At front ends of the front curved portions 11A and 11A, the right and left inner compressed grooves 11 and 11 are connected to each other through a front connecting compressed groove 12. The front connecting compressed groove 12 is curved toward the front end edge 1c.

From boundaries between the front curved portions 11A and 11A and the front connecting compressed groove 12, extension compressed grooves 13 and 13 are further extended toward the front end edge 1c. The extension compressed grooves 13 and 13 are disposed symmetrically about the longitudinal centerline Oy-Oy. The extension compressed grooves 13 and 13 may extend in parallel with the longitudinal centerline Oy-Oy or extend such that separation distance therebetween gradually increases toward the front end edge 1c.

At rear ends of the rear oblique portions 11D and 11D, the inner compressed grooves 11 and 11 are connected to each other through a rear connecting compressed groove 14. The rear connecting compressed groove 14 is curved toward the rear end edge 1d.

Thus, the inner compressed grooves 11 and 11, the front connecting compressed groove 12, the extension compressed grooves 13 and 13 and the rear connecting compressed groove 14 are mutually connected. In addition, a given area of the skin surface of the sanitary napkin 1 is surrounded by the inner compressed grooves 11 and 11, the front connecting compressed groove 12 and the rear connecting compressed groove 14, and this surrounded area is referred to as central region 20. The central region 20 is of an elongated shape symmetrical about the longitudinal centerline Oy-Oy, wherein a portion forward of the lateral reference line Ox-Ox is shorter than a portion rearward of the lateral reference line Ox-Ox.

On both right and left sides of the central region 20, there are provided side regions where the liquid absorbent layer 4 is present. It should be noted that the inner compressed grooves 11 and 11 are not included in the side regions.

In the side regions, front outer compressed grooves 15 and 15 are disposed at positions spaced laterally apart from the front curved portions 11A and 11A of the inner compressed grooves 11 and 11. The front outer compressed grooves 15 and 15 are within a range having a given length forwardly and rearwardly from the lateral reference line Ox-Ox. The front outer compressed grooves 15 and 15 are curved similarly to the front curved portions 11A and 11A. More specifically, the separation distance between the front curved portion 11A and the front outer compressed groove 15 is uniform over the entire length of the front outer compressed groove 15.

At positions spaced laterally apart from the rear oblique portions 11D and 11D of the inner compressed grooves 11 and 11, on the other hand, there are disposed rear outer compressed grooves 16 and 16. The rear outer compressed grooves 16 and 16 includes opposing portions 16A and 16A that are generally parallel with the longitudinal centerline Oy-Oy and oblique portions 16B and 16B that are extended rearwardly continuously from the opposing portions 16A and 16A to gradually decrease separation distance therebetween toward the rear end edge 1d. Furthermore, rear ends of the rear outer compressed grooves 16 and 16 are connected to each other through a rear connecting compressed groove 17. The rear outer compressed grooves 16 and 16 and the rear connecting compressed groove 17 thus continuously formed are symmetrical about the longitudinal centerline Oy-Oy. Here, the rear connecting compressed groove 17 is curved toward the rear end edge 1d.

Rear ends 15A and 15A of the front outer compressed grooves 15 and 15 are located forward of the inflected portions 11B and 11B of the inner compressed grooves 11 and 11, whereas front ends 16D and 16D of the rear outer compressed grooves 16 and 16 are located rearward of the inflected portions 11B and 11B. Between the rear ends 15A and 15A and the front ends 16D and 16D, therefore, the front outer compressed grooves 15 and 15 are separated from the rear outer compressed grooves 16 and 16.

In the present embodiment, the side regions outside the inner compressed grooves 11 and 11 do not have outer compressed grooves within the range between the rear ends 15A and 15A and the front ends 16D and 16D, so that the rear ends 15A and 15A are longitudinally separated from the front ends 16D and 16D by a separation distance L1. The separation distance L1 is about 20 to 60 mm, as set forth above.

In addition, imaginary extensions Lh and Lh, which are extended in parallel with the longitudinal centerline Oy-Oy from the front ends 16D and 16D of the rear outer compressed grooves 16 and 16, more specifically, from the front ends 16D and 16D along width centers of the rear outer compressed grooves 16 and 16, intersect the inner compressed grooves 11 and 11. In the embodiment shown, the imaginary extensions Lh and Lh intersect the inflected portions 11B and 11B of the inner compressed grooves 11 and 11. In an alternative, the imaginary extensions Lh and Lh may intersect the rear oblique portions 11D and 11D of the inner compressed grooves 11 and 11.

The central region 20 includes a front central region 20A, an intermediate central region 20B, and a rear central region 20D. The intermediate central region 20B is within the area of the separation distance L1 between the rear ends 15A and 15A of the front outer compressed grooves 15 and 15 and the front ends 16D and 16D of the rear outer compressed grooves 16 and 16. The front central region 20A is within an area extending from a line between the rear ends 15A and 15A to the front connecting compressed groove 12; the rear central region 20D is within an area extending from a line between the front ends 16D and 16D to the rear connecting compressed groove 14. Of the intermediate central region 20B, a position between the inflected portions 11B and 11B, i.e., the portion where the separation distance between the inner compressed grooves 11 and 11 becomes largest is referred to as widened portion.

Regions of a uniform width between the front curved portions 11A and 11A of the inner compressed grooves 11 and 11 and the front outer compressed grooves 15 and 15 are first front side regions 21 and 21; regions positioned laterally outside the front outer compressed grooves 15 and 15 and having the liquid absorbent layer 4 therein are second front side regions 22 and 22. Regions positioned outside portions of the inner compressed grooves 11 and 11 which define the intermediate central region 20B therebetween are intermediate side regions 23 and 23. The intermediate side regions 23 and 23 are within the area of the separation distance L1.

Regions between the rear oblique portions 11D and 11D of the inner compressed grooves 11 and 11 and the rear outer compressed grooves 16 and 16 are first rear side regions 24 and 24; regions positioned laterally outside the rear outer compressed grooves 16 and 16 and having the liquid absorbent layer 4 therein are second rear side regions 25 and 25. In addition, a region positioned rearward of the rear end of the rear connecting compressed groove 14 but inside the rear outer compressed grooves 16 and 16 and the rear connecting compressed groove 17 is first rear region 26. On the other hand, a region positioned rearward of the rear end of the rear connecting compressed groove 14 but outside the rear outer compressed grooves 16 and 16 and the rear connecting compressed groove 17 and having the liquid absorbent layer 4 therein is second rear region 27.

In the central region 20, as shown in FIGS. 2, 4 and 5, a liquid guide layer 5 is provided between the topsheet 3 and the liquid absorbent layer 4. The liquid guide layer 5 is present only within the central region 20, without overlapping with the inner compressed grooves 11 and 11.

After the liquid absorbent layer 4, the liquid guide layer 5 and the topsheet 3 are stacked, the compressed groove 10, i.e., the distinct compressed grooves indicated by numerals 11-17 are embossed with a heating roller, and then the backsheet 2 is laid beneath the liquid absorbent layer 4 and bonded thereto through a hot-melt adhesive or the like.

In regions adjacent the front and rear end edges 1c and 1d, in which the liquid absorbent layer 4 does not exist as shown in FIG. 1, the backsheet 2 and the topsheet 3 are bonded together through a hot-melt adhesive or by heat-embossing. In regions adjacent the right and left side edges 1a and 1b, in which the liquid absorbent layer 4 does not exist either, on the other hand, the backsheet 2 and the topsheet 3 are likewise bonded together, and liquid-impermeable sheets 30 and 30 are laid on and bonded to the topsheet 3 and the backsheet 2 through a hot-melt adhesive, as shown in FIGS. 1, 2 and 4. The wings 1A and 1A and the rear flaps 1B and 1B are mainly composed of the backsheet 2 and the liquid-impermeable sheets 30.

As shown in FIGS. 2 and 4, the liquid-impermeable sheets 30 are folded in two with a plurality of elastically extensible members 32 interposed therebetween, wherein the confronting surfaces of the folded liquid-impermeable sheet 30 are bonded to each other so as to prevent the elastically extensible members 32 from slipping off. In front fixation regions 33 and 33, the liquid-impermeable sheets 30 thus folded in two are refolded and then bonded and fixed to the skin surface in such a folded state. Also in rear fixation regions 34 and 34, the liquid-impermeable sheets 30 are bonded and fixed to the skin surface in such a folded state. In FIG. 1, the front fixation regions 33 and 33 and the rear fixation regions 34 and 34 are indicated by hatching for the convenience of making clear their ranges in the drawing. The rear fixation region 34 is also shown in the sectional view of FIG. 4.

Between the front fixation regions 33 and the rear fixation regions 34, the liquid-impermeable sheets 30 and 30 are free within a given width, providing leakage preventing walls 31 and 31. The elastically extensible members 32 exert a longitudinal elastic shrinkage force on the leakage preventing walls 31 and 31. Front action ends 35 of the elastic shrinkage force are rear ends of the front fixation regions 33, while rear action ends 36 of the elastic shrinkage force are front ends of the rear fixation regions 34. The action ends 35 and the action ends 36 are attracted to each other due to the elastic shrinkage force, so that the sanitary napkin 1 is deformed with its skin surface slightly recessed within an area of a distance L2 between the action ends 35 and the action ends 36, as shown in FIG. 5. As a result, the leakage preventing walls 31 and 31 are raised from the skin surface within the area between the action ends 35 and the action ends 36, as shown in FIG. 2.

As shown in FIG. 1, the front action ends 35 are in the same longitudinal position as the boundaries between the inner compressed grooves 11 and the front connecting compressed grooves 12 or in the vicinity thereof. On the other hand, the rear action ends 36 are positioned rearward of the inflected portions 11B of the inner compressed grooves 11 but forward of the front ends 16D of the rear outer compressed grooves 16. Accordingly, the elastic shrinkage force of the elastically extensible members 32 mainly acts on an area including the intermediate central region 20B and the front central region 20A.

On the other hand, since the elastic shrinkage force does not act on a front potion where the extension compressed grooves 13 and 13 are present, the front portion can be certainly kept in a flat state. Similarly, since the elastic shrinkage force does not act on a rear portion where the rear outer compressed grooves 16 and 16 and the rear connecting compressed groove 17 are present, the rear portion can be certainly kept in a flat state.

Next, preferred materials for the individual components will be described.

The topsheet 3 may be a through-air bonded nonwoven fabric having a basis weight of about 25 g/m², wherein sheath/core bicomponent synthetic fibers, of which the core component is polyethylene terephthalate (PET) containing titanium oxide and the sheath component is polyethylene (PE), are bonded together by means of hot air. The basis weight of the topsheet 3 may vary from 15 to 60 g/m². If it is below the lower limit, the topsheet 3 may possibly break during use due to lack of sufficient surface strength. If it is above the upper limit, on the other hand, the topsheet 3 may possibly give a stiff feel to the wearer's body and therefore the wearer may feel uncomfortable in the crotch. In order to provide the topsheet 3 with excellent permeability to liquid, on the other hand, its density is preferably equal to or less than 0.12 g/cm³.

In an alternative, the topsheet 3 may be a spunbonded or spunlaced nonwoven fabric, a synthetic resin film with a large number of liquid passage holes, or a synthetic resin sheet formed in the shape of a net.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic sheet, followed by drawing. The film may have a thickness of about 15 to 50 μm.

The liquid absorbent layer 4 may be formed by adding synthetic absorbent polymer such as polyacrylate, polyacrylamide and maleic anhydride or natural absorbent polymer such as starch and cellulose to an aggregate of pulp such as ground pulp, mercerized pulp or crosslinked pulp, wherein the pulp and the synthetic absorbent polymer or the like are wrapped in hydrophilic tissue paper.

The liquid guide layer 5 may be a through-air bonded nonwoven fabric comprising eccentric sheath/core bicomponent synthetic fibers, of which the core component is polypropylene (PP) and the sheath component is polyethylene (PE), and having a density of 0.005 to 0.025 g/cm³. For example, the through-air bonded nonwoven fabric is prepared to have a basis weight of 20 g/m² and then used for the liquid guide layer 5 in three-ply construction.

In an alternative, the liquid guide layer 5 may be an air-laid nonwoven fabric, in which hydrophilic fibers such as pulp and rayon are accumulated in air, bonded together with a binder, and pressed with a heating roller, wherein the hydrophilic fibers may be optionally mixed with synthetic fibers. It is also possible to stack both the air-laid nonwoven fabric and the through-air bonded nonwoven fabric on the liquid absorbent layer 4 and cover them with the topsheet 3.

The liquid-impermeable sheet 30 for forming the leakage preventing wall 31 is a spunbonded nonwoven fabric, a meltblown nonwoven fabric or a lamination thereof, and is preferably treated to be water-repellent.

It should be noted that the above-mentioned components are bonded to each other through a hot-melt adhesive where necessary. In addition, the backsheet 2 has pressure-sensitive adhesive layers (not shown) on its exterior surface (i.e., garment surface). The pressure-sensitive adhesive layers are provided on a central portion of the sanitary napkin 1, as well as on the wings 1A, 1A and the rear flaps 1B, 1B.

Figure 6:
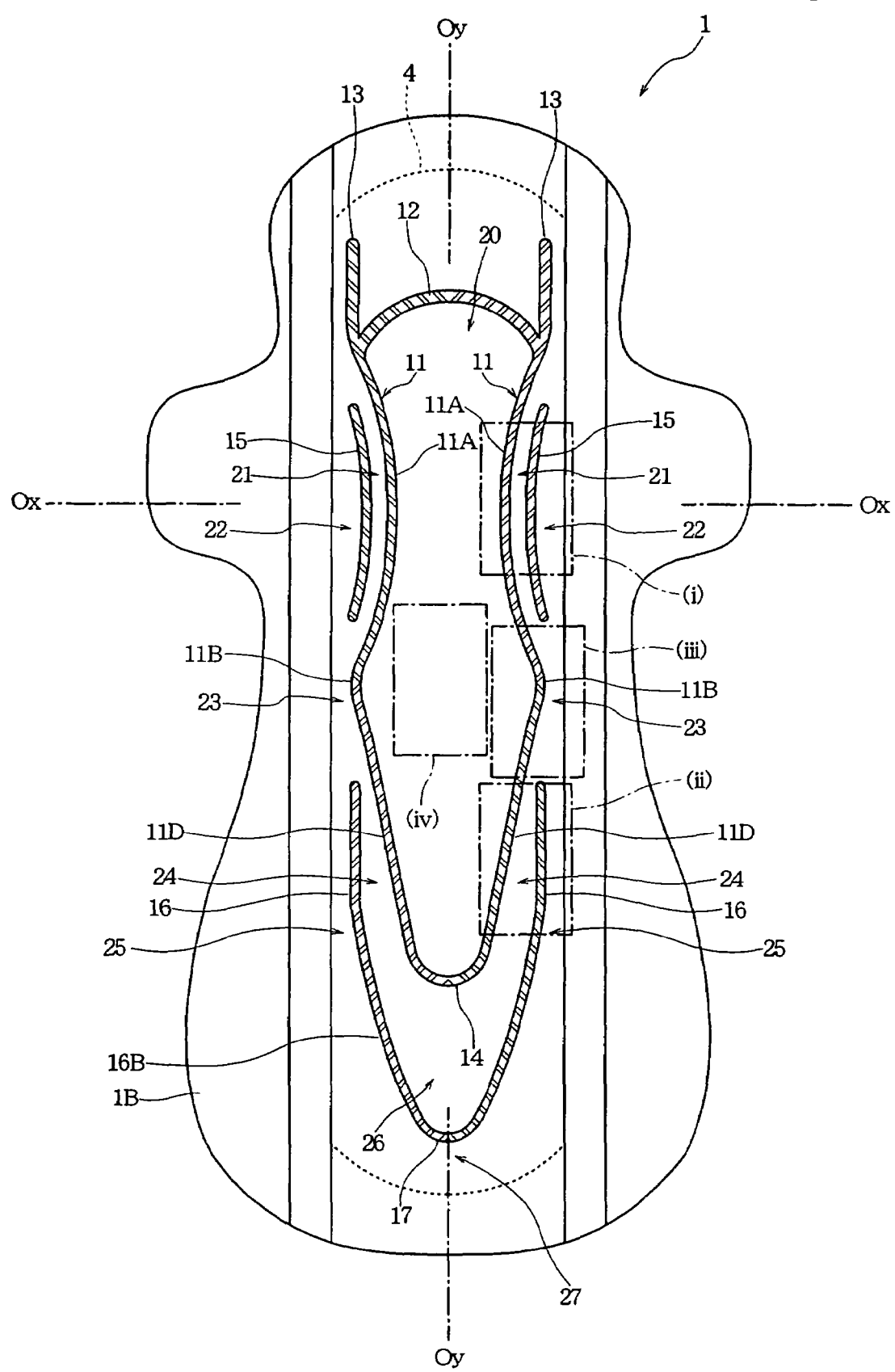
FIG. 6 is a top plan view of the sanitary napkin for describing properties of respective portions.

FIG. 6 is a view for describing properties of respective portions of the sanitary napkin 1. The drawing used for FIG. 6 is similar to that used for FIG. 1, but reference numerals are omitted except for portions necessary for description of the properties.

(1) Basis Weight of Liquid Absorbent Layer 4

The basis weight of the liquid absorbent layer 4 becomes highest at the central region 20, so that the basis weight of the liquid absorbent layer 4 is lower at the first front side regions 21, 21, the first rear side regions 24, 24 and the first rear region 26 than at the central region 20. Here, the basis weight of the liquid absorbent layer 4 at the remaining regions, i.e., at the region forward of the front connecting compressed groove 12, the second front side regions 22, 22, the intermediate side regions 23, 23, the second rear side regions 25, 25 and the second rear region 27 may be equal to, slightly higher than, or lower than that at the first front side regions 21, 21 and so on.

The basis weight of the liquid absorbent layer 4 at the central region 20 is preferably in the range of 400 to 1200 g/m², more preferably in the range of 500 to 1000 g/m². The basis weight of the liquid absorbent layer 4 at the first front side regions 21, 21, the first rear side regions 24, 24 and the first rear region 26 is preferably in the range of 300 to 900 g/m², more preferably in the range of 350 to 600 g/m². The basis weight of the liquid absorbent layer 4 at the region forward of the front connecting compressed groove 12, the second front side regions 22, 22, the intermediate side regions 23, 23, the second rear side regions 25, 25 and the second rear region 27 is preferably in the range of 300 to 500 g/m², but the upper limit may be 700 g/m², if required.

(2) Density of Liquid Absorbent Layer 4

The compressed grooves 11-17 shown in FIG. 6 are formed at a time by heat-embossing with the heating roller. As the topsheet 3 is pressed together with the liquid absorbent layer 4 at the front curved portions 11A, 11A and the front outer compressed grooves 15, 15, the density of the liquid absorbent layer 4 increases at the first front side regions 21, 21 due to tension given to portions of the topsheet 3 covering the first front side regions 21, 21.

If the embossing projections arranged on the surface of the heating roller are adapted to have shallow grooves between projections for forming the front curved portions 11A, 11A and projections for forming the front outer compressed grooves 15, 15, furthermore, the liquid absorbent layer 4 can be pressed with the shallow grooves at the first front side regions 21, 21 as the front curved portions 11A, 11A and the front outer compressed grooves 15, 15 are formed by pressing. In this case, therefore, the density of the liquid absorbent layer 4 can be increased more at the first front side regions 21, 21. Likewise, the density of the liquid absorbent layer 4 can be increased more at the first rear side regions 24, 24 between the rear oblique portions 11D, 11D and the rear outer compressed grooves 16, 16.

Also at the central region 20, slight tension is given to the topsheet 3 as the surrounding compressed grooves, i.e., the inner compressed grooves 11, 11, the front connecting compressed groove 12 and the rear connecting compressed groove 14 are formed, so that the density of the liquid absorbent layer 4 can be slightly increased at the central region 20.

Among the respective portions shown in FIG. 6, therefore, the density of the liquid absorbent layer 4 becomes highest at the first front side regions 21, 21. The density at the first rear side regions 24, 24 is preferably equal to that at the first front side regions 21, 21, but may be slightly lower than that at the first front side regions 21, 21. The density of the liquid absorbent layer 4 at the first rear region 26 is slightly lower than that at the first front side regions 21, 21 and the first rear side regions 24, 24. On the other hand, the density at the central region 20 is slightly lower than that at the first rear region 26, but may be equal to that at the first rear region 26.

It should be noted that the density of the liquid absorbent layer 4 at the region forward of the front connecting compressed groove 12, the second front side regions 22, 22, the intermediate side regions 23, 23, the second rear side regions 25, 25 and the second rear region 27 is lower than that at the other regions.

The density of the liquid absorbent layer 4 at the first front side regions 21, 21 and the first rear side regions 24, 24 is preferably in the range of 0.08 to 0.2 g/cm$^3$. On the other hand, the density of the liquid absorbent layer 4 at the central region 20 is preferably in the range of 0.05 to 0.18 g/cm$^3$. The density of the liquid absorbent layer 4 at the second front side regions 22, 22, the intermediate side regions 23, 23 and the second rear side regions 25, 25 is preferably in the range of 0.05 to 0.13 g/cm$^3$.

It should be noted that the density of the liquid absorbent layer 4 at the first front side regions 21, 21 is preferably higher than that at the central region 20 and that at the second front side regions 22, 22 and the intermediate side regions 23, 23 by at least 0.01 g/cm$^3$, more preferably, by at least 0.02 g/cm$^3$. Likewise, the density of the liquid absorbent layer 4 at the first rear side regions 24, 24 is preferably higher than that at the central region 20 and that at the second rear side regions 25, 25 and the intermediate side regions 23, 23 by at least 0.01 g/cm$^3$, more preferably, by at least 0.02 g/cm$^3$.

(3) Density of Compressed Groove 10

It is preferred that both the density of the high-density compressed portions 10a and the density of the medium-density compressed portions 10b fall within the range of 0.5 to 1.5 g/cm$^3$.

(4) Stiffness of Respective Portions

FIG. 6 shows sections of different bending stiffnesses in the sanitary napkin 1.

An area traversed by the front curved portion 11A of the inner compressed groove 11, the first front side region 21 and the front outer compressed groove 15 and overlapping with the central region 20 and the second front side region 22 is referred to as first section (i). An area traversed by the rear oblique portion 11D of the inner compressed groove 11, the first rear side region 24 and the rear outer compressed groove 16 and overlapping with the central region 20 and the second rear side region 25 is referred to as second section (ii). An area containing the inflected portion 11B of the inner compressed groove 11 and overlapping with the central region 20 and the intermediate side region 23 (but not overlapping with the front outer compressed groove 15 and the rear outer compressed groove 16) is referred to as third section (ii). An area located in the intermediate central region 20B but not overlapping with any compressed groove is referred to as fourth section (iv).

Hereinbelow, the relationship between the sections (i) to (iv) with respect to longitudinal bending stiffness will be described. It should be noted that the longitudinal bending stiffness means stiffness measured by bending the each respective section in the longitudinal direction of the sanitary napkin 1, wherein none of the components constituting sanitary napkin 1 is removed from the sections.

The bending stiffness becomes highest at the first section (i), and the second section (ii) is similar in bending stiffness to the first section (i). The bending stiffness is sufficiently lower in the third section (iii) than in the first section (i) and in the second section (ii). Furthermore, the bending stiffness is much lower in the fourth section (iv) than in the third section (iii).

The bending stiffness can be measured using a Gurley Bending Resistance Tester, wherein it is preferred that the first section (i) and the second section (ii) have a Gurley stiffness of 20 to 35 mN, the third section (iii) has a Gurley stiffness of 8 to 18 mN, and the fourth section (iv) has a Gurley stiffness of 3 to 8 mN.

The Gurley stiffness is preferably from 3 to 38 mN at ever part of the sanitary napkin. If it is equal to or greater than 3 mN, the sanitary napkin can stabilize in shape; if it is equal to or less than 38 mN, the sanitary napkin can be prevented from being excessively stiff and giving a stiff feel to the wearer's body.

The measurements of the Gurley stiffness are made on the each respective section having a width of 25 mm in the lateral direction (i.e., in a direction parallel with the lateral reference line Ox-Ox) and a length of 38 mm in the longitudinal direction, using a Gurley Flexibility Tester manufactured by YASUDA SEIKI SEISAKUSHO, LTD.

More specifically, the measurements of the Gurley stiffness are made in such a manner that after the sections (i) to (iv) are cut out of the sanitary napkin 1 to have a width of 25 mm in the lateral direction and a length of 38 mm in the longitudinal direction, bending test is performed with each sample brought into contact with a pendulum of the Gurley Flexibility Tester within a length of 6.3 mm from one end edge on the side of the rear end edge 1d while being held by a chuck within a length of 6.3 mm from the other end edge on the side of the front end edge 1c, wherein the average of the value measured for one bending direction in which the skin surface is pushed and the value measured for the other bending direction in which the garment surface is pushed is taken as the Gurley stiffness.

(5) Dimensions of Respective Portions

The length of the central region 20, i.e., the longitudinal distance between the front connecting compressed groove 12 and the rear connecting compressed groove 14 is about 120 to 300 mm. The width of the central region 20 on the lateral reference line Ox-Ox, i.e., the minimum width W1 of the front central region 20A shown in FIG. 2 is decided according to the width of the woman's genital organ. Because the crotch width of average women is about 30 mm, the width W1 is preferably in the range of 15 to 50 mm, more preferably in the range of 20 to 40 mm. On the other hand, the lateral distance between the inflected portions 11B, 11B of the inner compressed grooves 11, 11, i.e., the width of the widened portion of the intermediate central region 20B is larger than the width W1 by about 10 to 40 mm.

When measured in parallel with the longitudinal centerline Oy-Oy, the length of the front outer compressed grooves 15, 15 and the length of the first front side regions 21, 21 are both in the range of 30 to 120 mm. When measured in parallel with the lateral reference line Ox-Ox, the width of the first front side regions 21, 21 is preferably in the range of 5 to 15 mm, more preferably in the range of 5 to 10 mm. The minimum distance between the rear oblique portions 11D, 11D of the inner compressed grooves 11, 11 and the rear outer compressed grooves 16, 16 is also in the range of 5 to 15 mm.

It should be noted that the respective compressed grooves 11-17 have a width of about 0.5 to 3 mm.

Figure 7:
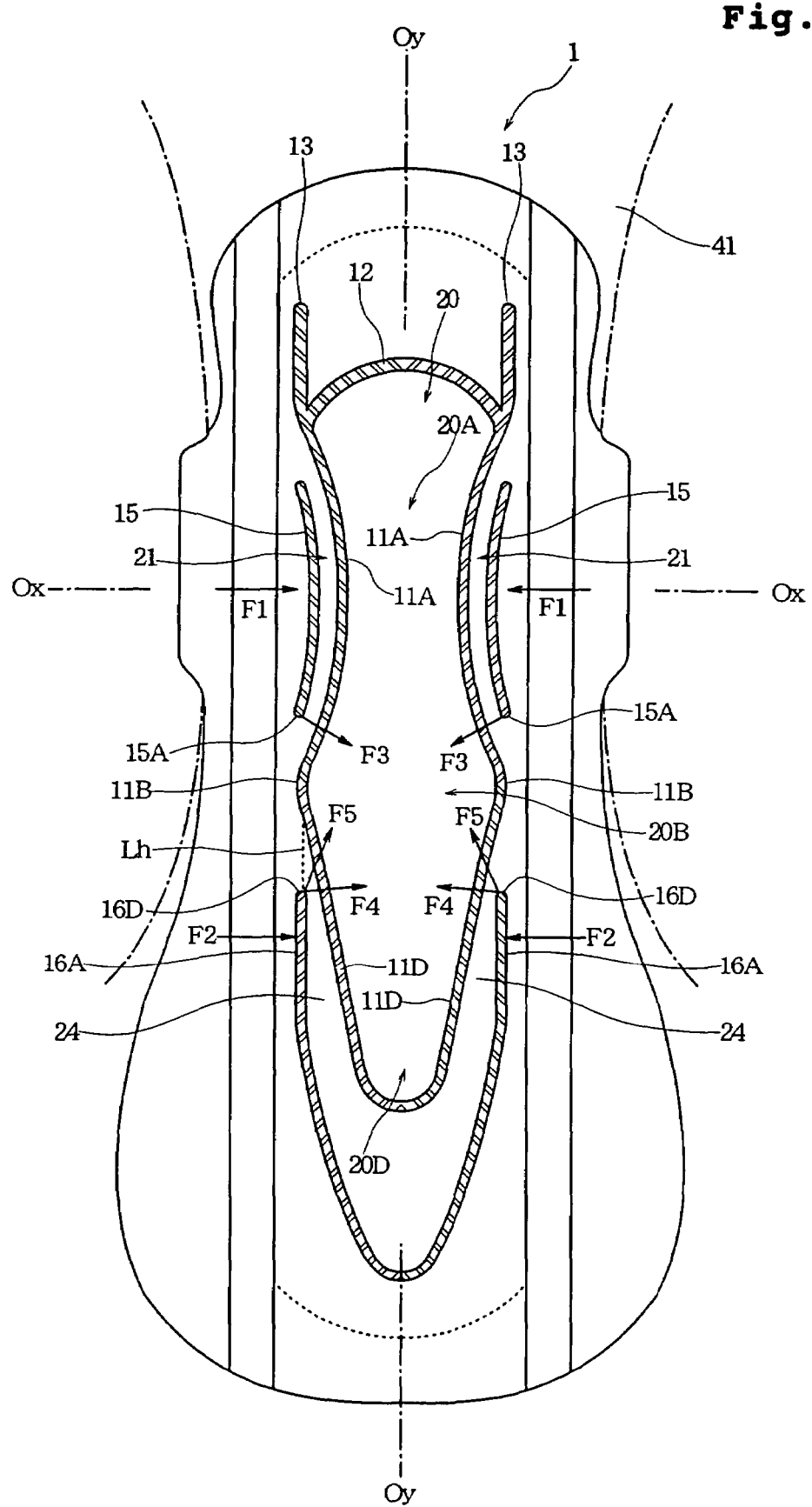
FIG. 7 is a top plan view in which the sanitary napkin attached to an undergarment is viewed from inside of the undergarment.

FIG. 2 is a sectional view showing a state where the sanitary napkin 1 is attached to an inner side of a groin piece 41 of an undergarment; FIG. 7 is a top plan view showing the sanitary napkin 1 attached to the groin piece 41 from inside of the undergarment.

When the sanitary napkin 1 is to be attached to the wearer's body, the pressure-sensitive adhesive layers provided on the exterior surface of the backsheet 2 is adhered to the inner side of the groin piece 41, and at this time, the rear flaps 1B, 1B are also adhered to the inner side of the groin piece 41. On the other hand, the wings 1A, 1A are folded back against an outer side of the undergarment to cover both side edges of the groin piece 41, and adhered to the outer side of the groin piece 41 through the pressure-sensitive adhesive layers provided on the garment surface of the wings 1A, 1A.

When the undergarment is worn with the sanitary napkin 1 attached to the groin piece 41 and the distance between thighs is narrowed while sleeping or during daytime activities, the thighs exert a compressive force F1, F1 toward the longitudinal centerline Oy-Oy on the front outer compressed grooves 15, 15, as shown in FIG. 7. The compressive force F1, F1 is transmitted to the first front side regions 21, 21 of a high density and a high stiffness via the front outer compressed grooves 15, 15, and further to the front curved portions 11A, 11A of the inner compressed grooves 11, 11.

As shown in FIG. 2, the front outer compressed grooves 15, 15 and the front curved portions 11A, 11A are located sufficiently below the midpoint of the thickness of the front central region 20A, and the first front side regions 21, 21 are also located sufficiently below the midpoint. Accordingly, when the compressive force F1, F1 is exerted, the front outer compressed grooves 15, 15, the first front side regions 21, 21 and the front curved portions 11A, 11A try to get under the front central region 20A, so that the front central region 20A is supported from below and raised up toward the wearer's body by the first front side regions 21, 21 of a high stiffness. Such deformation can bring the front central region 20A into close contact with the vaginal opening.

Likewise, a compressive force F2, F2 toward the longitudinal centerline Oy-Oy acts on the opposing portions 16A, 16A of the rear outer compressed grooves 16, 16. The compressive force F2, F2 is also exerted mainly by the approach of the thighs.

When the compressive force F2, F2 is exerted on the opposing portions 16A, 16A, the opposing portions 16A, 16A, the first rear side regions 24, 24 of a high density and the rear oblique portions 11D, 11D try to get under the rear central region 20D, so that the rear central region 20D is raised up toward the wearer's body by the first rear side regions 24, 24 of a high stiffness as in the deformation of the front portion shown in FIG. 3. Thus, the rear central region 20D tends to fit into the recess near the anus and the cleft of the buttocks.

Next, the intermediate central region 20B will be described. As has been described hereinabove, the third section (iii) shown in FIG. 6 has a lower stiffness than portions positioned forward and rearward thereof. Forward of the third section (iii) of a lower stiffness, as shown in FIG. 7, the rear ends 15A, 15A of the front outer compressed grooves 15, 15 (i.e., rear ends of the first sections (i) of a higher stiffness) subjected to the compressive force F1, F1 exert a compressive force F3, F3 toward the longitudinal centerline Oy-Oy. Since portions of the inner compressed grooves 11, 11, to which the rear ends 15A, 15A of the front outer compressed grooves 15, 15 are opposed, are rearwardly inclined away from the longitudinal centerline Oy-Oy, the compressive force F3, F3 has force components perpendicular to the portions of the inner compressed grooves 11, 11.

Similarly, the front ends 16D, 16D of the rear outer compressed grooves 16, 16 (i.e., front ends of the second sections (ii) of a higher stiffness) subjected to the compressive force F2, F2 exert a compressive force F4, F4 toward the longitudinal centerline Oy-Oy, and the compressive force F4, F4 also has force components perpendicular to the rear oblique portions 11D, 11D of the inner compressed grooves 11, 11.

The intermediate central region 20B has the widened portion between the inflected portions 11B and 11B, and the compressive forces F3, F3 and F4, F4 act on the front and rear portions of the widened portion from four directions. As described above, the compressive forces F3, F3 and F4, F4 have force components that concentrate near the center of the intermediate central region 20B, and additionally, the action points of the respective compressive forces are located sufficiently below the midpoint of the thickness of the intermediate central region 20B (i.e., located closer to the backsheet 2). Since the fourth section (iv) within the intermediate central region 20B and the third sections (ii) at both sides thereof are of a relatively low stiffness, when the compressive forces are exerted from four directions to concentrate at a lower position, the inner compressed grooves 11, 11 serve as flexible hinges so that the intermediate central region 20B is raised up toward the wearer's body as if it were picked up from four directions with the inflected portions 11B and 11B positioned therebetween.

Figure 10:
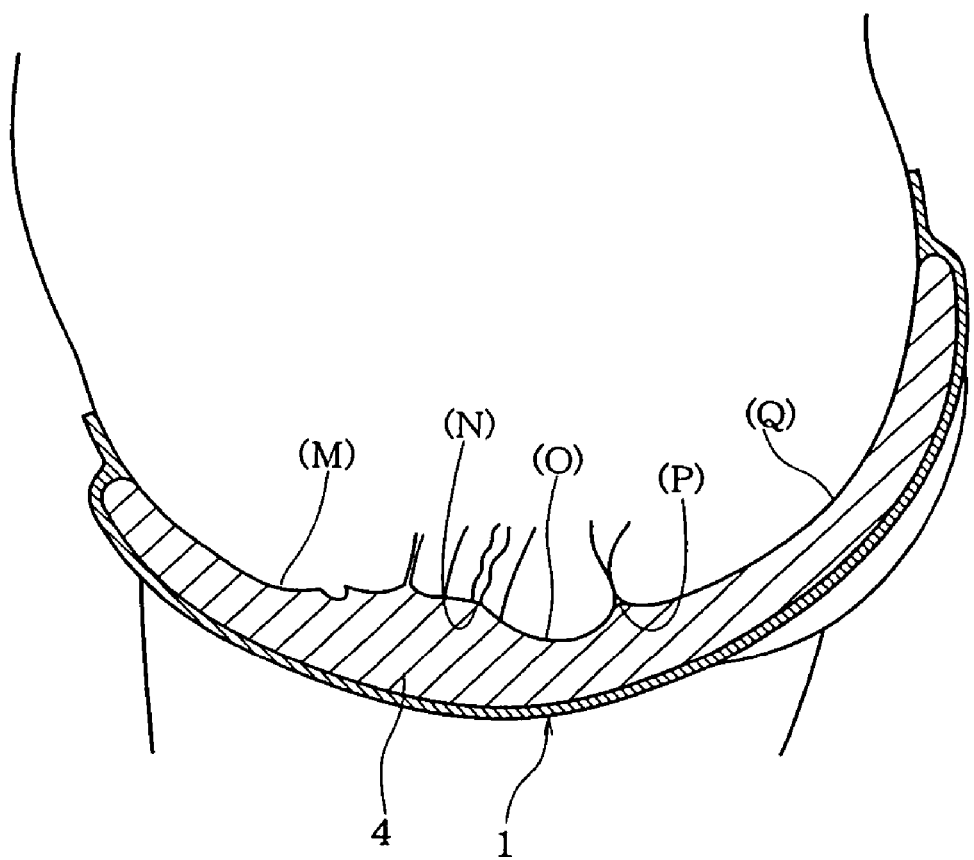
FIG. 10 is a sectional view showing a state where the sanitary napkin is applied to the wearer's body.

Inside the undergarment, furthermore, the sanitary napkin 1 is longitudinally curved with its garment surface so bulged as to conform to the contour of the wearer's body, as shown in FIG. 10. Since the skin surface of the sanitary napkin 1 is compressed at this time, the front ends 16D, 16D of the rear outer compressed grooves 16, 16 tend to approach the rear ends 15A, 15A of the front outer compressed grooves 15, 15. That is, the second sections (ii) that are highly stiff and located rearward of the intermediate central region 20B tend to approach the first sections (i) that are located forward thereof but also highly stiff.

At this time, a compressive force F5, F5 is exerted on the intermediate central region 20B from behind as shown in FIG. 7, and the compressive force F5, F5 is supported by the first sections (i). Since the compressive force F5, F5 acts on both sides of the intermediate central region 20B, deformation occurs such that the intermediate central region 20B is folded to project toward the wearer's body, wherein its ridge is shaped to extend along the longitudinal centerline Oy-Oy and pressed against the wearer's body.

As shown in FIG. 1, the action ends 35 and 36 of the elastically extensible members 32 which exert an elastic shrinkage force on the leakage preventing walls 31, 31 are located at longitudinally opposite sides with the intermediate central region 20B positioned therebetween. Therefore, the elastic shrinkage force of the elastically extensible members 32 also functions to add to the compressive force F5, F5.

It should be noted that since the basis weight is almost uniform in the central region 20 and the intermediate central region 20B is wider than the front and rear regions, the volume is larger in the intermediate central region 20B than in the front and rear regions of the central region 20. When deformed by receiving the compressive forces F3, F4 and F5, therefore, the bulging amount of the intermediate central region 20B toward the wearer's body is increased, so that the surface of the intermediate central region 20B can project more toward the wearer's body than the front central region 20A.

FIG. 10 is a sectional view showing the outline of the woman's crotch to which the sanitary napkin 1 is applied.

In the woman's crotch, the vaginal opening (N) is located posterior to the mons pubis (M), and the vaginal opening (N) is deeply recessed at a position between the labia majora. The crotch is outwardly bulged from the vaginal opening (N) to the perineum (O) and then shallowly recessed near the anus (P). The cleft (Q) of the buttocks extends continuously rearwardly therefrom.

When the sanitary napkin 1 is worn, the front central region 20A deformed into the state of FIG. 3 enters the recess between the labia majora to fit on the vaginal opening (N). In addition, since the intermediate central region 20B subjected to the forces concentrating from four directions bulges toward the wearer's body, as set forth above, the intermediate central region 20B can fit on the perineum (O) and into the groove of the labia majora anterior to it, as well as into the recess near the anus posterior to the perineum (O).

Furthermore, the rear central region 20D can fit into the recess near the anus (P) and the cleft (Q) posterior to it, wherein since the width of the rear central region 20D gradually decreases toward the rear end edge 1$d$, the rear central region 20D easily enters the cleft (Q) of the buttocks and hardly gives an uncomfortable feel to the wearer's body after the entry.

Menstrual blood discharged from the vaginal opening (N) is given to the front central region 20A and absorbed. Menstrual blood trying to flow rearwardly along the wearer's crotch or the topsheet 3 of the sanitary napkin 1 in a lying posture or the like is blocked by contact between the intermediate central region 20B and the perineum (O), and menstrual blood thus blocked is mainly absorbed by the liquid absorbent layer 4 in the intermediate central region 20B. Thus, the menstrual blood can be prevented from migrating from the anus (P) to the cleft (Q), so that the rearward leakage of menstrual blood can be effectively prevented.

Moreover, the elastic shrinkage force of the elastically extensible members 32 provided in the leakage preventing walls 31 acts between the action ends 35 and the action ends 36, as shown in FIG. 1, whereas the elastic shrinkage force does not act on the portion forward of the action ends 35 and the portion rearward of the action ends 36. Therefore, since the portion forward of the front connecting compressed groove 12 can be kept flat while being allowed to be folded at the extension compressed grooves 13, 13, this portion can easily fit on the mons pubis (M). Likewise, the portion rearward of the action ends 36 can also be kept flat so as to cover a large area of the buttocks.

Still furthermore, the intermediate central region 20B and the intermediate side regions 23, 23 are of a low stiffness, the portion positioned forward of them and intended to fit in the wearer's crotch is of a high stiffness due to the presence of the first sections (i), and the portion positioned rearward of the intermediate side regions 23, 23 and intended to cover the wearer's buttocks is of a high stiffness due to the presence of the second sections (ii). In the sanitary napkin 1, therefore, the intermediate central region 20B and the intermediate side regions 23, 23 can function as deformable boundaries, so that the front portion fitting in the wearer's crotch and the rear portion covering the wearer's buttocks can move independently from each other. Accordingly, even if displacement occurs in a positional relation between the front portion fitting in the wearer's crotch and the rear portion covering the wearer's buttocks due to a change in posture while sleeping or the like, the displacement in position can be absorbed by deformation of the intermediate central region 20B and the intermediate side regions 23, 23. As a result, the sanitary napkin 1 can be certainly prevented from twisting or deforming as a whole.

Figure 8:
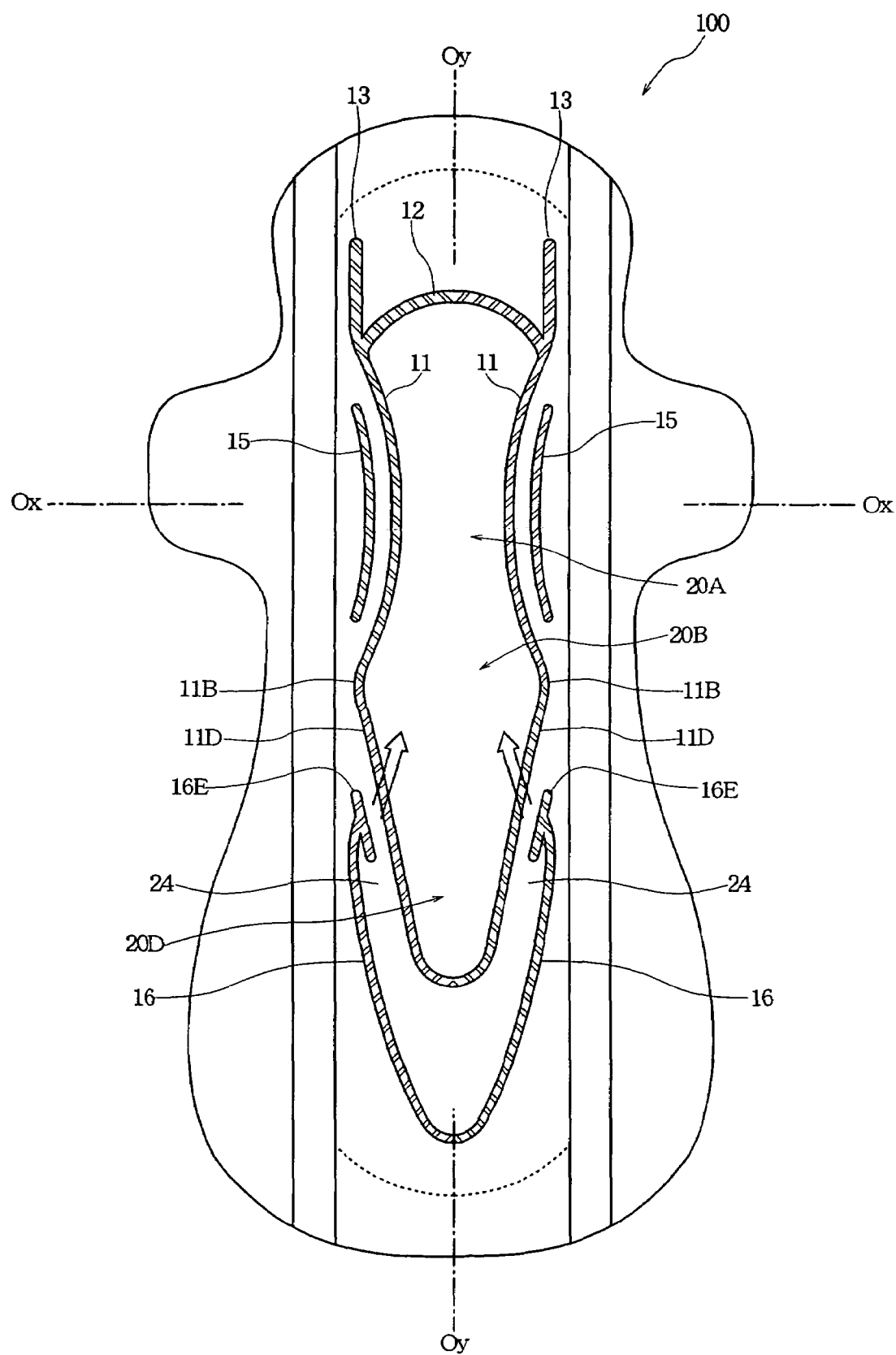
FIG. 8 is a top plan view showing a sanitary napkin according to a second embodiment of the present invention.

FIG. 8 is a top plan view showing a sanitary napkin 100 according to a second embodiment of the present invention. In this second embodiment, the rear outer compressed grooves 16 are different in shape from those shown in FIG. 1, but the other constructions and shapes are identical to those of the embodiment shown in FIG. 1.

In the embodiment of FIG. 8, short, front end-abutting portions 16E, 16E are disposed at the front ends of the rear outer compressed grooves 16, 16 to extend substantially parallel with the rear oblique portions 11D, 11D of the inner compressed grooves 11, 11. In this embodiment, when the compressive forces F4, F4 and F5, F5 shown in FIG. 7 are exerted, the front end-abutting portions 16E, 16E get under the rear oblique portions 11D, 11D of the inner compressed grooves 11, 11 to raise the rear portion of the intermediate central region 20B high toward the wearer's body, wherein the raised intermediate central region 20B is supported from the side of the backsheet 2 by the front end-abutting portions 16E, 16E.

This results in further improvement in contact between the intermediate central region 20B and the perineum and its surroundings.

Figure 9:
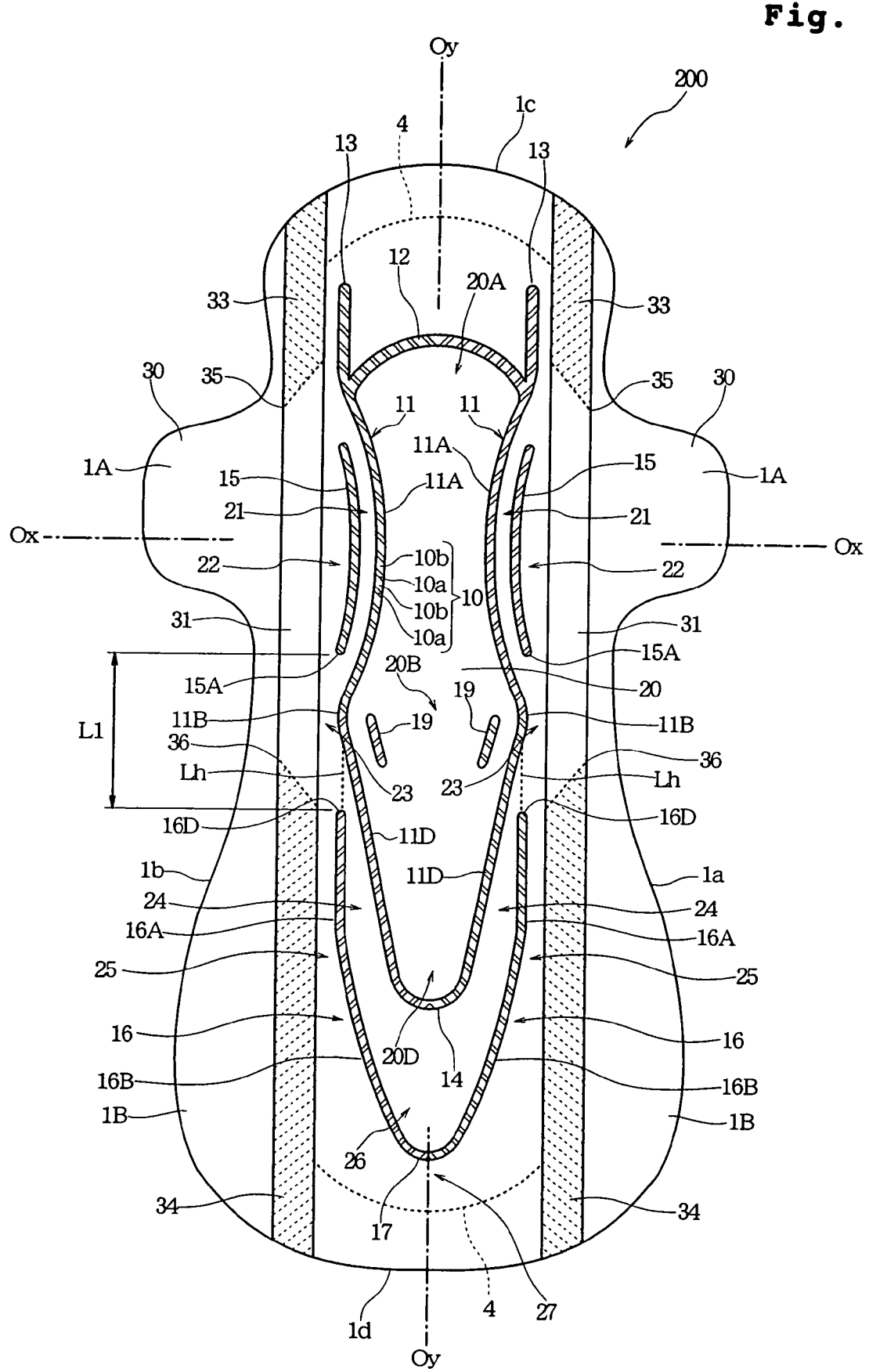
FIG. 9 is a top plan view showing a sanitary napkin according to a third embodiment of the present invention.

FIG. 9 is a top plan view showing a sanitary napkin 200 according to a third embodiment of the present invention.

In the sanitary napkin 200, short compressed grooves 19, 19 are disposed between the inflected portions 11B, 11B, i.e., in the rear portion of the intermediate central region 20B. This embodiment has the same basic shape and construction as the first embodiment of FIG. 1, except for the short compressed grooves 19, 19. Therefore, the detailed description of the portions having the same shape and construction as those of the first embodiment of FIG. 1 will be omitted by designating them by the common reference numerals.

In the short compressed grooves 19, 19 of the sanitary napkin 200, the high-density compressed portions 10$a$ and the medium-density compressed portions 10$b$ alternate with each other and the liquid absorbent layer 4 is compressed together with the topsheet 3, as in the other compressed grooves 11-17.

The short compressed grooves 19, 19 are disposed symmetrically about the longitudinal centerline Oy-Oy, wherein the separation distance between the short compressed grooves 19, 19 gradually rearwardly decreases, as in the rear oblique portions 11D, 11D. It should be noted that the short compressed grooves 19, 19 are located within the range L1 between the rear ends 15A of the front outer compressed grooves 15 and the front ends 16D of the rear outer compressed grooves 16.

As shown in FIG. 7, the intermediate central region 20B receives the compressive forces F3, F3 and F4, F4 from four directions at the front and rear portions of the inflected portions 11B, 11B and further receives the longitudinal compressive force F5, F5 from the rear outer compressed grooves 16, 16. At this time, since the short compressed grooves 19, 19 are within the intermediate central region 20B, the intermediate central region 20B receiving the compressive forces from the respective directions can be inhibited from being widened laterally, and in addition, since the short compressed grooves 19, 19 can function as longitudinally extending flexible hinges, the intermediate central region 20B can easily be bulged to have a longitudinally extending ridge. As a result, the intermediate central region 20B can certainly fit on the perineum and portions anterior and posterior to it.

It is to be understood that the present invention should not be understood as limited to the specific embodiments set forth above, but various changes may be made therein.

For example, the right and left inner compressed grooves 11 and 11 and the right and left rear outer compressed grooves 16 and 16 may be independent each other without providing the front connecting compressed groove 12, the rear connecting compressed groove 14 and the rear connecting compressed groove 17.

In the intermediate side regions 23, 23 between the rear ends 15A, 15A of the front outer compressed grooves 15, 15 and the front ends 16D, 16D of the rear outer compressed grooves 16, 16, on the other hand, there may be provided embossed portions that are so small that the stiffness is not excessively increased.

In the central region 20, on the other hand, the topsheet 3 may be apertured to have a large number of liquid passage holes or corrugated to have ribs and grooves alternating with each other. Particularly in the intermediate central region 20B and the rear central region 20D, a bulky cushion layer such as through-air bonded nonwoven fabric may be disposed between the topsheet 3 and the liquid absorbent layer 4, in addition to the liquid guide layer 5. This will result in further improvement in contact between the intermediate central region 20B and the perineum.

If the topsheet 3 is corrugated to have longitudinally extending ribs and grooves at least partially in each of the intermediate central region 20B, the front central region 20A and the rear central region 20D, furthermore, the topsheet 3 can be laterally stretched when one of these regions is deformed to bulge toward the wearer's body so as not to provide a resistance to the deformation, and as a result, the deformation toward the wearer's body can be made large.

In the present invention, as long as the inner compressed grooves 11, 11 are provided and the stiffness is lower in the third section (iii) than in the first and second sections (i) and (ii), the intermediate central region 20B can be raised up toward the wearer's body during wear. If the above-mentioned conditions are satisfied, the front outer compressed grooves 11, 11 and the rear outer compressed grooves 16, 16 may be omitted. In this case, for example, the stiffness may be increased in both the sections (i) and (ii) by increasing the density of the liquid absorbent layer 4 at positions outside the inner compressed grooves 11, 11 or members such as foamed material and paper for reinforcing the stiffness may be provided at positions outside the inner compressed grooves 11, 11.

According to the present invention, as has been described hereinabove, since the intermediate central region can be certainly raised up toward the wearer's body to come into close contact with the perineum and so on, migration of menstrual blood rearwardly from the front central region can be blocked to effectively prevent rearward liquid leakage. In addition, since the absorbent article can easily follow the movement of the wearer's body while sleeping, it is hardly twisted or wrinkled.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An elongated absorbent article having a lateral reference line on which the absorbent article is intended to face an wearer's vaginal opening during use, the absorbent article comprising:
    a garment surface having a backsheet;
    a skin surface having a topsheet, and provided with inner and outer compressed grooves; and
    a liquid absorbent layer provided between the topsheet and the backsheet, the liquid absorbent layer being recessed together with the topsheet at the inner and outer compressed grooves, wherein
    the inner and outer compressed grooves are positioned symmetrically about a longitudinal centerline of the absorbent article,
    the inner compressed grooves include a pair of inner compressed grooves each extending across the lateral reference line and curving to form a laterally bulging portion at a rear side from a lateral reference line,
    a lateral distance between the inner compressed grooves decreases forwardly from the laterally bulging portion toward the lateral reference line, and decreases rearwardly from the laterally bulging portions,
    the outer compressed grooves are positioned apart from the inner compressed grooves and in side regions outside a central region defined by the inner compressed grooves,
    the outer compressed grooves include a pair of front outer compressed grooves positioned at a forward side from the laterally bulging portions of the inner compressed grooves, and a pair of rear outer compressed grooves positioned at a rear side from the laterally bulging portions of the inner compressed grooves,
    each of the front outer compressed groove extends across and symmetrically about the lateral reference line,
    each of the rear outer compressed groove extends in a direction of the longitudinal centerline of the absorbent article with a front end thereof spaced apart rearwardly from a rear end of each of the front outer compressed groove, respectively, and the front and rear outer compressed grooves increase density of the liquid absorbent layer so that each side region has a relatively low stiffness at a portion located adjacent the laterally bulging portion of the inner compressed groove and between the rear end of the front outer compressed groove and the front end of the rear outer compressed groove.

2. The elongated absorbent article as set forth in claim 1, wherein imaginary extensions extending forward from the front ends of the rear outer compressed grooves in parallel with the longitudinal centerline intersect the laterally bulging portions of the inner compressed grooves.

3. The elongated absorbent article as set forth in claim 1, wherein the absorbent article is intended to face an wearer's perineum during use on a line extending between the laterally bulging portions of the inner compressed grooves.

4. The elongated absorbent article as set forth in claim 1, wherein elastic members are disposed symmetrically about the longitudinal centerline to exert a longitudinal elastic shrinkage force across the laterally bulging portions of the inner compressed grooves.

5. An elongated absorbent article having a lateral reference line on which the absorbent article is intended to face an wearer's vaginal opening during use, the absorbent article comprising:
   a garment surface having a backsheet;
   a skin surface having a topsheet, and provided with inner and outer compressed grooves; and
   a liquid absorbent layer provided between the topsheet and the backsheet, the liquid absorbent layer being recessed together with the topsheet at the inner and outer compressed grooves, wherein
   the inner compressed grooves include a pair of inner compressed grooves positioned symmetrically about a longitudinal centerline of the absorbent article, each extending across the lateral reference line and curving to form a laterally bulging portion at a rear side from a lateral reference line,
   a lateral distance between the pair of inner compressed grooves decreases forwardly from the laterally bulging portion toward the lateral reference line, and decreases rearwardly from the laterally bulging portions, the outer compressed grooves are positioned symmetrically about the longitudinal centerline of the absorbent article, apart from the inner compressed grooves, and in side regions outside a central region defined by the inner compressed grooves, the outer compressed grooves include a pair of front outer compressed grooves and a pair of rear outer compressed grooves, the pair of front outer compressed grooves are positioned at a forward side from the laterally bulging portions of the inner compressed grooves, and each extended across and symmetrically about the lateral reference line, and the pair of rear outer compressed grooves positioned at a rear side from the laterally bulging portions of the inner compressed grooves, each extended in a direction of the longitudinal centerline of the absorbent article with a front end thereof spaced apart rearwardly from a rear end of each of the pair of front outer compressed groove, respectively.

6. An elongated absorbent article, comprising:

a garment surface having a backsheet;

a skin surface having a topsheet and provided with inner and outer compressed grooves; and a liquid absorbent layer provided between the topsheet and the backsheet, wherein the inner and outer compressed grooves are positioned symmetrically about a longitudinal centerline of the absorbent article, the outer compressed grooves are positioned in side regions outside a central region defined by the inner compressed grooves, and the outer compressed grooves include front and rear outer compressed grooves that are spaced apart from each other in a direction of the longitudinal centerline of the absorbent article.

* * * * *